(12) United States Patent
Weathers et al.

(10) Patent No.: US 9,055,989 B2
(45) Date of Patent: Jun. 16, 2015

(54) LOW-SPLASH REDUCING IMPLEMENT FOR DENTAL APPLICATIONS

(71) Applicants: Arthur Kitchings Weathers, Scottsdale, AZ (US); T. Wilfred Pye, Lindale, GA (US)

(72) Inventors: Arthur Kitchings Weathers, Scottsdale, AZ (US); T. Wilfred Pye, Lindale, GA (US)

( * ) Notice: Subject to any disclaimer, the term of this patent is extended or adjusted under 35 U.S.C. 154(b) by 0 days.

(21) Appl. No.: 13/986,557

(22) Filed: May 14, 2013

(65) Prior Publication Data

US 2014/0342308 A1   Nov. 20, 2014

(51) Int. Cl.
*A61C 3/025* (2006.01)
*A61C 1/00* (2006.01)
*A61C 1/08* (2006.01)

(52) U.S. Cl.
CPC ............ *A61C 3/025* (2013.01); *A61C 1/0061* (2013.01); *A61C 1/081* (2013.01)

(58) Field of Classification Search
CPC ....... A61C 3/025; A61C 1/0061; A61C 1/081
USPC ............. 433/80–90; 222/330, 410, 411, 326, 222/327, 401, 386, 400.8, 137, 52, 61, 626, 222/478, 190, 630
See application file for complete search history.

(56) References Cited

U.S. PATENT DOCUMENTS

| | | | | |
|---|---|---|---|---|
| 2,442,033 A * | 5/1948 | Brantly et al. | | 433/82 |
| 5,800,367 A * | 9/1998 | Saxer et al. | | 601/164 |
| 6,164,967 A * | 12/2000 | Sale et al. | | 433/80 |
| 7,080,980 B2 * | 7/2006 | Klupt | | 433/80 |
| 2002/0004188 A1 * | 1/2002 | Beerstecher et al. | | 433/88 |
| 2012/0141953 A1 * | 6/2012 | Mueller | | 433/88 |

* cited by examiner

*Primary Examiner* — Ralph Lewis

(57) ABSTRACT

The invention is a low-splash dental fluid distribution implement with the ability to evenly wear down tooth decay, diseased tissue, or undesired dentin in oral applications with live patients. The directed multi-beams of pressurized fluid are a combined plurality of individual beams paired in such a manner that the reflected fluid bursts are inwardly directed against each other. This canceling effect prevents damage to the oral tissues of the patient's mouth by curtailing outward bound bursts of fluid arising from the initial directed impact. Also, the outer edges of the strike zone receive a comparable force as that which hits the center.

8 Claims, 5 Drawing Sheets

LOW-SPLASH REDUCING IMPLEMENT FOR DENTAL APPLICATIONS

BACKGROUND OF THE INVENTION

The treatment of dental caries in all manner of decay possibilities is done with the objective of removing undesired layers of active decay, minimizing future bacterial intrusions, and filling the excavated site with appropriate fillings. Unfortunately, dentists employing the accepted method of high-speed drilling will inevitably and consistently remove far more undamaged dentin than is desirable. Secondly, they will introduce by the very nature of drill action a layer of potential bacterial corruption called the smear zone. This is where the rotating and grinding of the drill tip ceases to dig further, leaving a rough landscape which dentists must attempt to polish away. Mechanically drilling away caries and tooth structure is a remedy to a problem, but a process found lacking in many ways.

The use of abrasive air or fluid driven methodology to resolve medical problems is centered on anatomical features undergoing gross exposure to reducing substances flung against them. Any attempt in the prior art to limit fluid bounce or splash is centered on physical barrier shields to contain rebounding discharges. It is directly due to damage to peripheral tissue that the use of pressurized fluids in dental applications is primarily used for low psi cleaning applications, rather than cavity care. A liquid jet stream brings a force of impact against dental structure that is concentrated in the center, with less proportional force the further from this center that is measured. Although capable of cleaning surfaces, this singular type of stream is not optimal for evenly wearing away dental structures in the zone hit by the fluid. Thus in these examples the outer edge of the strike zone (relative to the center) is not removed with a similar depth. With reducing elements included, the result is a curved-wall crater rather than a flat and round pill-box style excavation.

SUMMARY OF THE INVENTION

The invention is a low-splash dental fluid distribution implement with the ability to evenly wear down tooth decay, diseased tissue, or undesired dentin in oral applications with live patients. The directed multi-beams of pressurized fluid are a plurality of individual beams paired in such a manner that the reflected fluid bursts are inwardly directed against each other. This canceling effect prevents damage to the oral tissues of the patient's mouth by curtailing outward bound bursts of fluid arising from the initial directed impact. Also, the outer edges of the impact zone receive a comparable force as that which strikes the center. The dentist has adjustable control over both the intensity and distribution field of the pressurized sterile fluid, which may contain a pre-determined amount of reductive elements held in suspension. The desired result is the severe reduction in cratering, gouging, and non-symmetrical damage introduced by implements of the prior art such as drills, jet-stream fluid delivery systems, and tissue sanders with less danger of tongue and gum damage to the patient in these cases of comparison.

It is an objective of the instant invention to severely reduce the potentially harmful splashing after-effects of a pressurized beam of fluid directed against teeth.

It is another objective of the instant invention to provide a dental implement capable of delivering a plurality of circularly-moving bursts of fluid against dental structure with the objective to reduce all of said structure in an even fashion within the strike zone, such that the reduction has a diameter roughly equal to the diameter of the collective whole of the individual bursts and a uniform depth across the entire strike zone.

It is another objective of the instant invention to provide a dental implement capable of low-pressure levels below 120 psi for released fluid.

It is another objective of the instant invention to provide a dental implement that is not stifled in its ability to erode hard calcified tooth tissue.

It is another objective of the instant invention to provide a dental implement capable of significantly reducing the generation of cratering and smear zone regions as engendered by procedures to remove dental structure within a field of operation (such as encompassed by entire dental decay cavity), where the field diameter is much wider and larger than the momentary impact zone of a prior art drill or liquid jet.

It is another objective of the instant invention to provide a dental implement capable of significantly reducing the elevated patient discomfort offered by prior art drilling techniques, and reducing the need for needle-injection deadening of nerve responses to prevent or lower such patient discomfort.

DETAILED DESCRIPTION OF THE INVENTION

Figure 1:
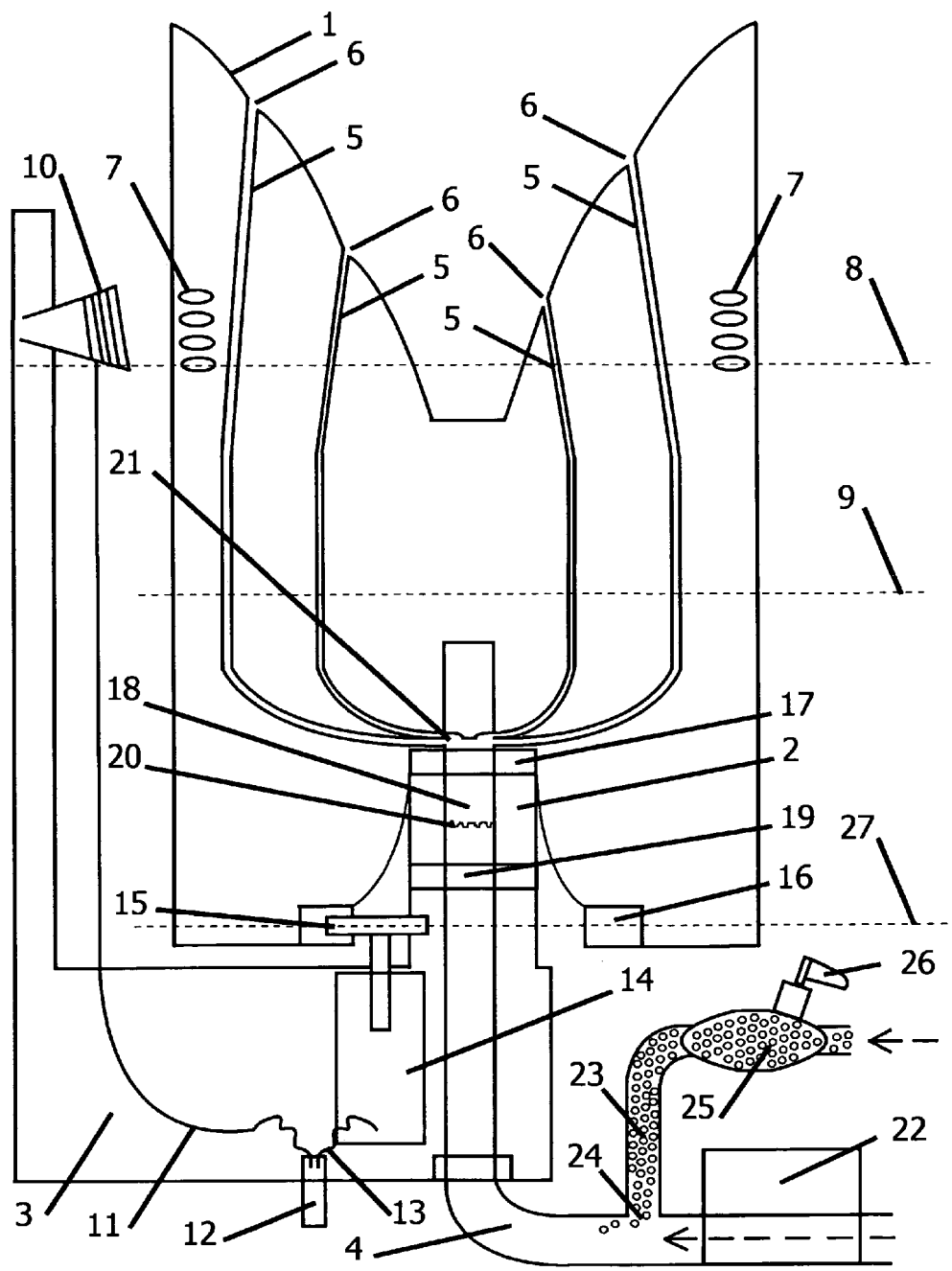
FIG. 1 is a side view of oral fluid-delivery emitter (1) coupled to the fluid release end of a water rotary union (2). The union (2) is itself coupled to a stabilizing fixture (3) which secures an input channel (4) delivering pressurized fluidic medium. The delivery end is cone-indented; a shape that releases the heavier outer beams closer to the target. The stabilizing fixture can be snap-fitted by design onto a standard dental hand piece (not shown).
Figure 5:
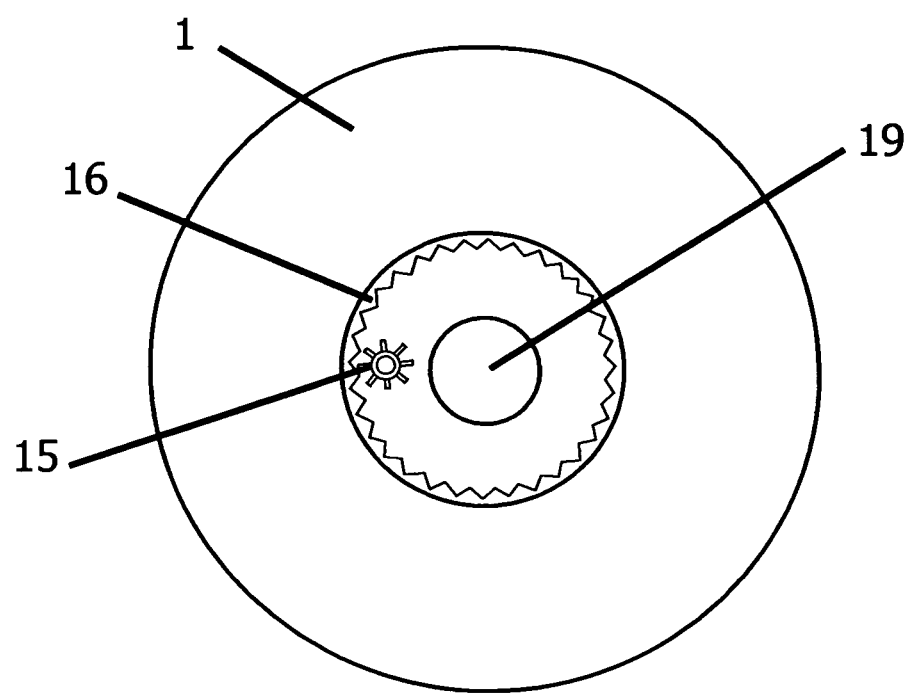
FIG. 5 is a cross-section view of gear (15) engaging spokes (16) of emitter (1). This enables the process whereby emitter (1) spins as it releases fluid directed against a substrate. Centrally located entry pipe (19) carries fluid and does not spin.

FIG. 1 is a side cut-away view of the fluid-delivery emitter (1). There is a plurality of fluid channels (5) gently sloping inward to the center direction as they terminate at a release opening (6). Small polarized magnets (7) are near the outer side boundaries. These magnets (7) are aligned alike, such that the North ends all point in the same direction; either in towards the central axis, or away from the axis. Hashed line (8) isolates a cross-section that will be depicted in FIG. 4 to clarify this. Hashed line (9) harkens a region of emitter (1)

that is manufactured from a soft plastic similar to that used for plastic tubing. Thus, the release end of emitter (1) can be pulled to, or pushed away from, a variable strength polarized magnetic field generator (10) attached to an arm of stabilizing fixture (3). Operator control reversing the polarity of field generator (10) either pulls or repels the magnets (7) embedded in the spinning outer edge of emitter (1), which either pulls or repels the entire release end of emitter (1), causing a bending effect allowed by the elasticity of the middle region of emitter (1). Electrical current is supplied to field generator (10) by wire (11), which enters stabilizing fixture (3) at electrical connector (12). Additional wire (13) supplies electricity to a small motor (14) securely fastened to fixture (3). When energized, motor (14) spins its toothed gear (15). The teeth of gear (15) engage complementary spokes (16) lining the inside lower end of emitter (1), which causes emitter (1) to spin around on command. Water union (2) has a release end (17) that spins together with exit fluid pipe (18). However, entry pipe (19) passes fluid delivered in by input channel (4) on through to exit pipe (18), as is the innate utility of water unions. The junction (20) of pipe (18) and pipe (19) is fashioned to contain leaks while fluid is being passed from one pipe to the other. Nexus (21) is the position along pipe (18) where the fluid is routed into the plurality of channels (5). Pressurized fluid delivered through stabilizing fixture (3) is initially routed through solenoid valve (22), which alternately stops and releases the inflow as programmed. A desired operational value would engage multiple times a second, which causes fluid microbursts to leave each release opening (6), rather than continuous micro jets. Pressurized gas (23) is mixed with incoming fluid at crossing junction (24) after passing through gas entry valve (25). Operator control of regulation lever (26) sets the amount of pressurized gas admixed with the incoming fluid. Hashed line (27) isolates a cross-section of the lower end of emitter (1) as depicted in FIG. 5.

Figure 2:
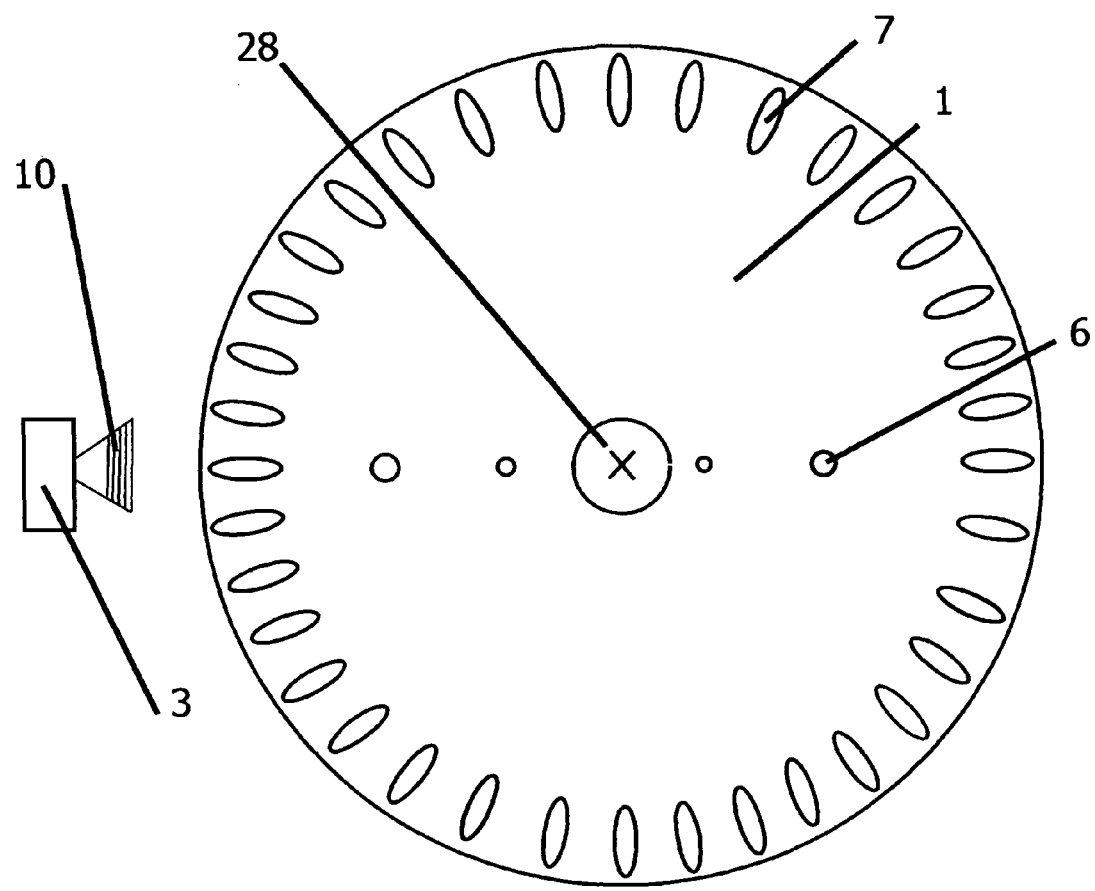
FIG. 2 is an end perspective view down into the delivery end of emitter (1) showing several fluid release openings (6) and showing the ring of polarized magnets (7) used for sweeping the entire end of emitter (1) in a predetermined rapid back and forth fashion.

FIG. 2 is an end perspective view of emitter (1), which spins around central axis (28), which is further identified by the letter "X". The plurality of release openings (6) are each placed at varying distances from axis (28). The further a particular release opening is from axis (28), there is an increase in diameter. This increases the volume of fluid released at the outer edges of emitter (1), and lessens the relative volume of fluid released in the central regions when emitter (1) is spinning. To further evenly distribute the entire discharge across a desired target surface, a polarized ring of small magnets (7) can be attracted or repulsed from polarized magnetic field generator (10), which is immobile because it is attached to stabilizing fixture (3). Because the central torso region (9) of emitter (1) is somewhat flexible, the entire fluid discharge is swept back and forth at high speed to inundate the target dental surface. This happens as the polarity of generator (10) is reversed from North attracting to North repulsing by operator programming.

Figure 3:
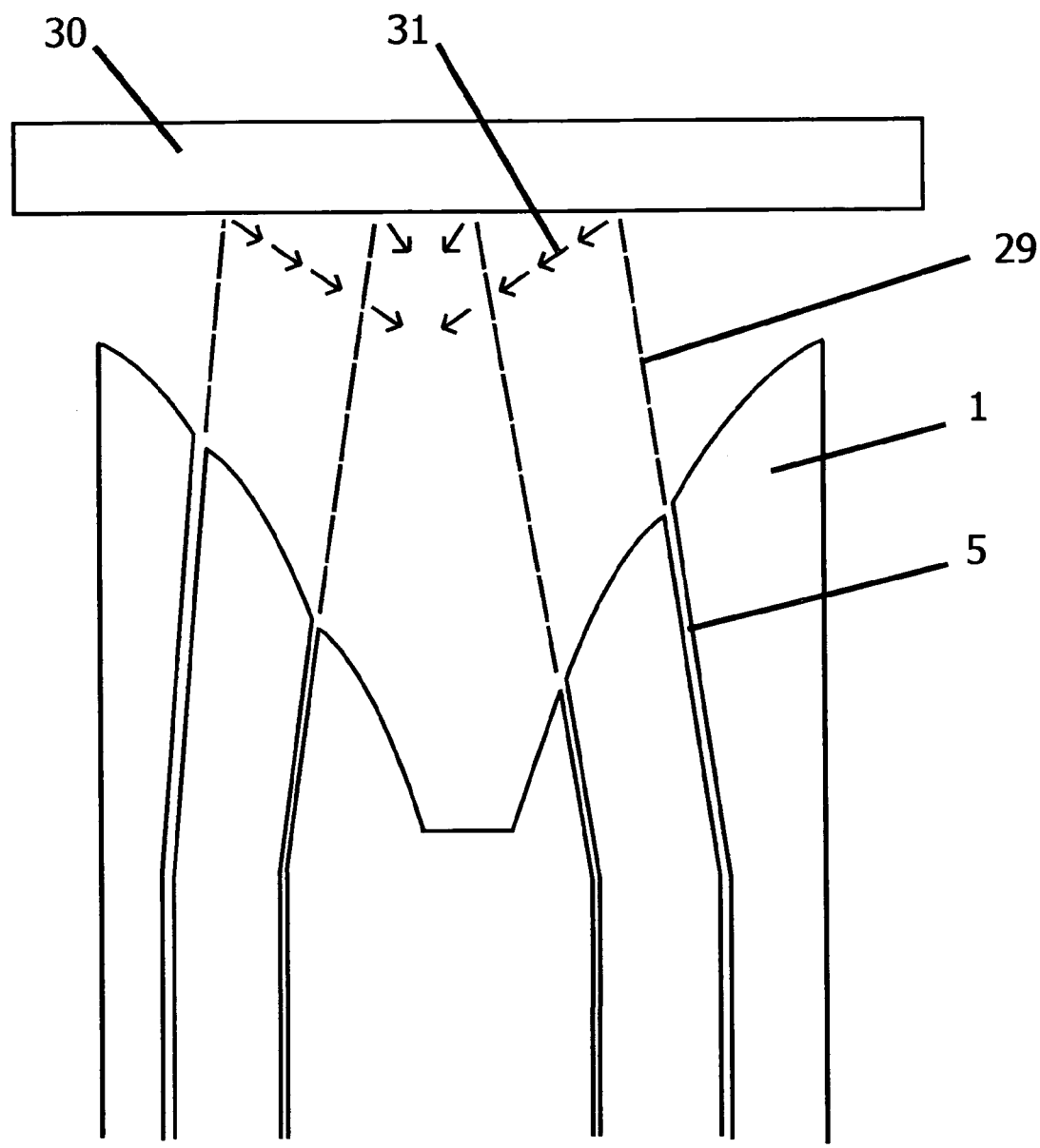
FIG. 3 is a side partial view of the anterior end of microburst emitter (1) delivering a plurality of fluid discharges (29) to a chosen dental surface (30). Reflected fluid (31) bounces inwards to a point where it collides with a counter reflected shower from an opposing stream of discharges. This greatly reduces outward splatter onto undesired areas of the patient's soft mouth tissue.

FIG. 3 is a side view of the discharge end of emitter (1) showing the effect of directing the fluid channels (5) to an inwards slope angle. Ejected fluid (29) from channel (5) strikes a juxtaposed target surface (30) flush on, which causes the majority of deflected splash (31) to head towards the inner spin axis. This splash (31) is designed to be nullified and lose further impact strength as it collides with a counter splash from an opposing channel of emitter (1). This nullification effect, as the emitter spins, severely limits the outwards splash created by the overall fluid impacting a target surface.

Figure 4:
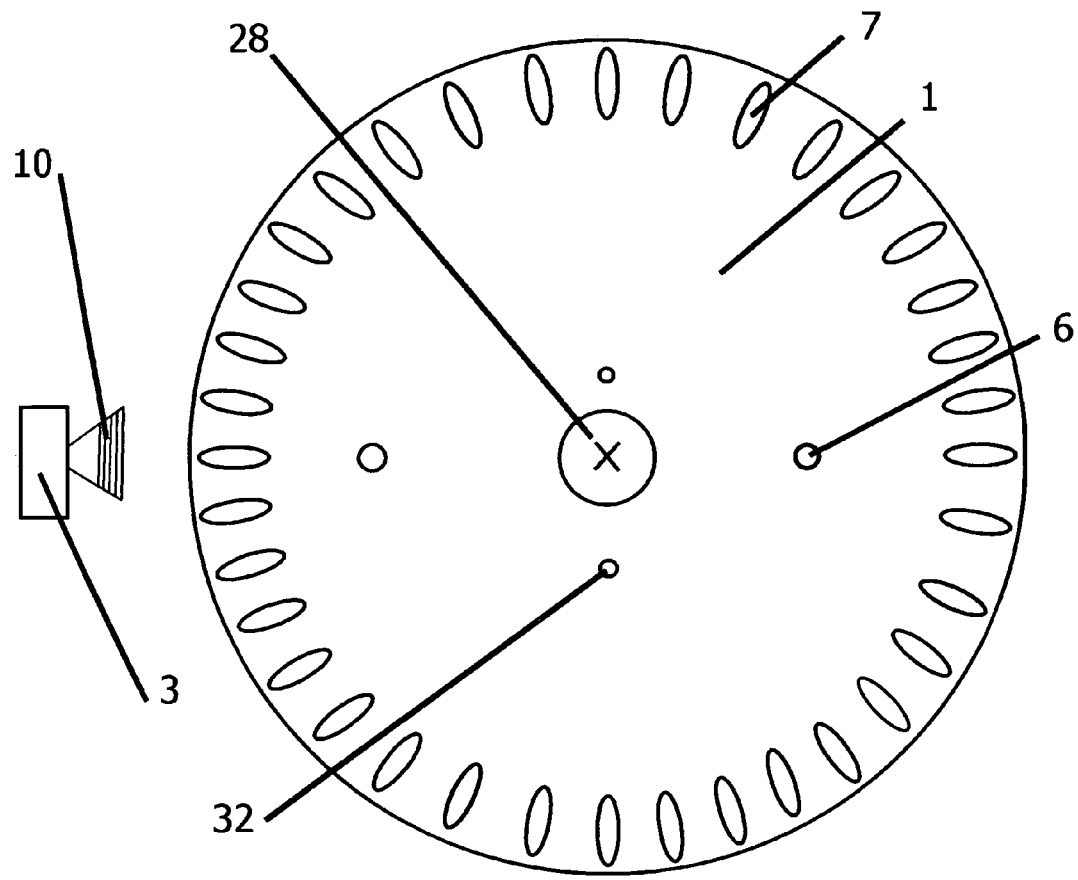
FIG. 4 is an end perspective view similar to FIG. 2, whereby the innermost paired openings are rotated 90 degrees to the line derived through the outermost paired release openings. This is the paired release opening orientation of the preferred embodiment when fitted with 4 release channels.

FIG. 4 is an end perspective view of emitter (1) similar to that of FIG. 2, where one of the innermost pair of release openings (32) together with its paired nullification partner, are moved to a 90 degree position from the linear orientation of the two outermost openings. This is the release opening orientation of the preferred embodiment. A 90 degree orientation reduces the chance of splashed fluid from the outermost pair of release openings blocking the incoming flight of fluid from the innermost pair of openings, as is depicted in FIG. 3 where four release openings are arranged in perfect linear fashion.

FIG. 5 is a cross section along section line (27) as seen in FIG. 1. This shows the propulsion of emitter (1) into a steady spin by the action of motor-driven gear (15) engaging a ring of matching spokes (16) encircling the inner lower portion of emitter (1). Delivery pipe (19) does not spin, and holds a central location as fluid pass through it up into spinning emitter (1).

SUMMATION

The preferred instant invention is a low-splash fluid distribution implement that spins around a central axis for fluid elongation. Its discharge is unlike a single jet of water which continually drives fluid onto fluid. As a result of the spin-induced elongation effect, the paired inward-sloping beams from the instant invention continually strike substrate before splashing towards each other. An improvement is the addition of a sweep action to the discharge. Further dependent improvements to the invention include water mass reduction by both use of a solenoid valve (22) and aeration. The latter by admission of gas particles to the fluid stream at a crossing junction (24).

Means to laterally sweep the discharge end of the emitter are described using magnetic attraction and repulsion. This feature is termed lateral displacement sweeping. Other patterns can be created. For example, another magnetic field generator placed 90 degrees from the first could cross-sweep the emitter's release end in tandem with the original displacement pattern. This combined sweeping motion is termed circular displacement sweeping. Other travel patterns and sweep schemes than magnetic can be designed.

The described electric motor (14) and gear (16) used in FIG. 1 to propel the emitter can be replaced by air driven motors, magnetic circuits, or other propulsion technology known to the art.

The instant invention can be applied to other categories within dentistry such as removing tartar, orthodontic adhesive, or old bonding layers for porcelain cap re-fittings, etc, or other fields such as veterinarian medicine.

The foregoing description of the preferred and alternate embodiments of the invention has been presented for purposes of illustration and description. It is not intended to be exhaustive or to limit the invention to the precise form disclosed, as many modifications and variations are possible in light of the above teaching without deviating from the spirit and the scope of the invention. The embodiments described are selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

We claim:

1. A low-splash dental fluid distribution implement, comprising: an emitter, a water union, a stabilizing fixture, a polarized magnetic field generator attached firmly to said stabilizing fixture, a source of pressurized fluid, and means to rotate said emitter attached to said stabilizing fixture;

said stabilizing fixture with an input channel to receive said pressurized fluid from a delivery channel fluidly coupled to said source of pressurized fluid;

said emitter fluidly coupled to said water union;

said water union fluidly coupled to said stabilizing fixture;

said emitter containing a plurality of paired channels open to carry, direct, and release said pressurized fluid;

said paired channels sloping inwards towards the central axis of said emitter; resulting in the separate simultaneous discharge of said pressurized fluid from said paired channels, whereby upon striking flush on a juxtaposed surface said simultaneous discharges deflect back into each other in a splash nullification process;

said emitter further including a middle section constructed of semi-flexible material;

with the end release section of said emitter fitted with a series of polarized magnets at the outer surface enclosing the circumference of said emitter; resulting in the magnetic shift by said generator of the position of said end release section by the compliant bending of said semi-flexible material.

2. A fluid distribution implement as in 1, wherein said means to rotate said emitter comprises a geared motor.

3. A fluid distribution implement as in 1, further comprising a solenoid; said solenoid fluidly coupled between said input channel of said stabilizing fixture and said pressurized fluid source; resulting in said solenoid controlling the delivery of said fluid to said entry port.

4. A fluid distribution implement as in 1, wherein said pressurized fluid contains reductive elements.

5. A fluid distribution implement as in 1, further comprising a crossing junction fitted into said input channel, and a source of pressurized gas fluidly coupled to said crossing junction; resulting in the mixture of said pressurized gas through said crossing junction with said pressurized fluid.

6. A fluid distribution implement as in 1, whereby the release openings of any of said paired channels of said emitter lie in a straight line, and are not in the same straight line containing another of said paired channels.

7. A fluid distribution implement as in 1, with the line through a given pair of said release channels oriented 90 degrees from a second line through a second pair of said release channels.

8. A fluid distribution implement as in 1, whereby the release openings of said paired channels of said emitter lie at different distances from the spin axis of said emitter, and the inner diameter of an individual channel is greater than for another individual channel placed closer to said spin axis; wherein the release end of said emitter comprises a cone-indented shape.

* * * * *